(12) United States Patent
Miyahara et al.

(10) Patent No.: US 10,231,909 B2
(45) Date of Patent: *Mar. 19, 2019

(54) α-GEL-INTERMEDIATE COMPOSITION, AND PRODUCTION METHOD FOR α-GEL-CONTAINING O/W EMULSION COSMETIC USING SAID COMPOSITION

(71) Applicant: SHISEIDO COMPANY, LTD., Tokyo (JP)

(72) Inventors: Reiji Miyahara, Yokohama (JP); Tetsuro Yonezawa, Yokohama (JP); Kenji Kurokawa, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/317,798

(22) PCT Filed: May 28, 2015

(86) PCT No.: PCT/JP2015/065435
§ 371 (c)(1),
(2) Date: Dec. 9, 2016

(87) PCT Pub. No.: WO2015/190306
PCT Pub. Date: Dec. 17, 2015

(65) Prior Publication Data
US 2017/0105909 A1 Apr. 20, 2017

(30) Foreign Application Priority Data
Jun. 13, 2014 (JP) .................................. 2014-122250

(51) Int. Cl.
*A61K 8/06* (2006.01)
*A61K 8/34* (2006.01)
(Continued)

(52) U.S. Cl.
CPC ................ *A61K 8/062* (2013.01); *A61K 8/06* (2013.01); *A61K 8/34* (2013.01); *A61K 8/342* (2013.01);
(Continued)

(58) Field of Classification Search
None
See application file for complete search history.

(56) References Cited

U.S. PATENT DOCUMENTS

| 8,182,827 B2 | 5/2012 | Okamoto et al. |
| 9,102,842 B2 | 8/2015 | Shinoda et al. |

(Continued)

FOREIGN PATENT DOCUMENTS

| EP | 2 387 985 | 11/2011 |
| EP | 2 548 549 | 1/2013 |

(Continued)

OTHER PUBLICATIONS

Paul, Bidyut K., and Satya P. Moulik. "Uses and applications of microemulsions." Current science (2001): 990-1001. (Year: 2001).*

(Continued)

*Primary Examiner* — Nissa A Westerberg
(74) *Attorney, Agent, or Firm* — Andrew F. Young, Esq.; Lackenbach Siegel, LLP

(57) ABSTRACT

The present invention provides an intermediate composition enabling to prepare easily and steadily an α-gel-containing O/W emulsion cosmetic that has a very small viscosity change over time and is excellent in emulsion stability, without using a cooling device that has a heavy burden on cost and the environment, and a production method thereof. An α-gel intermediate composition consisting of (A) 20 to 80 mass % of a mixture containing one or more higher alcohols having 16 or more carbon atoms and an anionic surfactant in the mole ratio of 3:2 to 5:1, and (B) 20 to 80

(Continued)

A mixture of behenyl alcohol:sodium N-stearoyl methyl taurine = 3:1 forms α-gel in water mass % of a mixture containing one or more water-soluble solvents having the IOB value of 1.5 to 3.5 and water in the mass ratio of 5:5 to 8:2, and wherein the composition is a liquid consisting of a bicontinuous microemulsion phase or a lamellar liquid crystal-dispersed bicontinuous microemulsion phase at 65 to 85° C. and a solid at room temperature.

2 Claims, 5 Drawing Sheets

(51) Int. Cl.
  *A61K 8/44* (2006.01)
  *A61K 8/55* (2006.01)
  *A61K 8/46* (2006.01)
  *A61Q 17/04* (2006.01)
  *A61Q 19/00* (2006.01)
(52) U.S. Cl.
  CPC ............ *A61K 8/345* (2013.01); *A61K 8/44* (2013.01); *A61K 8/46* (2013.01); *A61K 8/466* (2013.01); *A61K 8/55* (2013.01); *A61Q 17/04* (2013.01); *A61Q 19/00* (2013.01); *A61K 2800/10* (2013.01); *A61K 2800/49* (2013.01)

(56) References Cited

U.S. PATENT DOCUMENTS

| 2004/0077735 | A1* | 4/2004 | Okamoto | A61K 8/042 516/53 |
|---|---|---|---|---|
| 2006/0024256 | A1 | 2/2006 | Wells et al. | |
| 2006/0269501 | A1 | 11/2006 | Johnson et al. | |
| 2010/0048442 | A1* | 2/2010 | Kawano | A61K 8/31 510/159 |
| 2011/0274731 | A1 | 11/2011 | Miyahara | |
| 2012/0164086 | A1 | 6/2012 | Araki | |

FOREIGN PATENT DOCUMENTS

| JP | 59-046123 | 3/1984 |
|---|---|---|
| JP | H02-51665 | 11/1990 |
| JP | 3829048 | 12/2001 |
| JP | 3829048 | 7/2006 |
| JP | 2009-518559 | 5/2009 |
| JP | 2010 006716 | 1/2010 |
| JP | 4709320 | 3/2011 |
| JP | WO 2011/027811 | 3/2011 |
| JP | 5047369 | 7/2012 |
| JP | 2013-116884 | 6/2013 |

OTHER PUBLICATIONS

Kunieda, Hironobu, et al. "Spontaneous formation of highly concentrated water-in-oil emulsions (gel-emulsions)." Langmuir 12.9 (1996): 2136-2140. (Year: 1996).*
Lindman, Björn, et al. "On the demonstration of bicontinuous structures in microemulsions." Colloids and Surfaces 38.1 (1989): 205-224. (Year: 1989).*
EP 15807126.6, European Search Report dated Nov. 29, 2017, 7 pages—English.
PCT/JP2015/065435, International Search Report and Written Opinion dated Sep. 1, 2015, 4 pgs.—Japanese, 1 pgs.—English.
Toru Okamoto, "Keshohin no Kiban Gijutsu kara Manabu Seizai Gijutsu Dai 6 Kai a-Gel to O/W Cream"; Pharm Tech Japan, Dec. 1, 2006 (Dec. 1, 2006), vol. 22, No. 13, pp. 85-89.
Yoshikazu Konno, "Denkaishitsu Kyozon-kei Deno O/W Emulsion Seizal no Kaihatsu", Franagrance Journal, Apr. 26, 2005 (Apr. 26, 2005), special extra issue No. 19, pp. 90-95.
JP 2015-108435, Office Action and translation, dated Aug. 27, 2016—3 pgs.—Japanese, 3 pgs.—English.
JP 2015-108435, Cited Reference 1, dated Aug. 18, 2015, 8 pgs.—Japanese; 1 pg.—English.
JP 2015-108435, Cited Reference 2, dated Aug. 18, 2015, 8 pgs.—Japanese, 1 pg.—English.
Yakugaku Zasahi, vol. 104, No. 9, pp. 986-989, 1894.
Toshiyuki Suzuki, Journal of SCCJ, vol. 44, No. 2, pp. 103-117, 2010.
"Physical Chemsitry of Cetyl Alcohol" by Fukushima, Fragrance Journal Ltd., pp. 79-83, 1992.
"Latest Functional Creation/Material Development/Applied Technology for Cosmetics", by Abe, Suzuki and Fukui, Gijutsu Kyoiku Shuppansha, pp. 238-241, 2007.
"Systematic Organic Qualitative Analysis (Edition for Mixtures)", by Fujita and Akatsuka, by Shuppan Co. Ltd., 1974.
PCT/JP2015/065435, International Preliminary Report on Patentability dated Dec. 15, 2016, 6 pages—English, 6 pages—Japanese.
U.S. Appl. No. 15/317,753, Office Action dated Feb. 8, 2018, 17 pages.
U.S. Appl. No. 15/317,753, Response to Office Action dated Apr. 16, 2018.
PCT/JP2015/065434, International Search Report and Written Opinion, dated Sep. 1, 2015, 7 pages—Japanese; 5 pages—English, COT.
Toru Okamoto, "Keshohin no Kiban Gijutsu kara Manabu Seizai Gijutsu Dai 6 Kai a-Gel to O/W Cream", Pharm Tech Japan, Dec. 1, 2006 (Dec. 1, 2006), vol. 22, No. 13, pp. 85-89, 1 pg. English.
PCT/JP2015/065434, Japanese Patent Claims, 1 pg.—Japanese, 2 pgs.—English.
JP 2015-108436, Notification of Reasons for Refusal dated Aug. 18, 2015, 3 pgs—English, 3 pgs—Japanese.
JP 2015-108436, Written Argument dated Oct. 21, 2016, 1 pg.—Japanese, 1 pg.—English.
Fukushima, Yoshida, Yamaguchi, "Internal Structure of Oil-in-Water Emulsion Stabilized with a Cetostearyl Alcohol", vol. 104, No. 9, pp. 986-989, dated Feb. 24, 1984, NII—Electronic Library Service.
Toshiyuki Suzuki, "Preparation Technology based on the Basic Cosmetic Technology", Journal of SCCJ, vol. 44, No. 2, No. 13, pp. 103-117, dated 2010.
"Physical Chemistry of Cetyl Alcohol", Shoji Fukushima, published by Fragrance Journal Ltd., pp. 79-83, dated 1992.
"Latest Functional Creation/Material Development/Appplied Technology for Cosmetics", by Masahiko Abe, Toshiyuki Suzuki and Hiroshi Fukui, published by Gijutsu Kyoiku Shuppansha, pp. 238-241, dated 2007.
EP 15807292.8, European Search Report dated Oct. 5, 2017, 8 pages—English.
"Correlation of physical parameters of an oil in water emulsion with manufacturing procedures and stability", by U.T. Lashmar, J.P. Richardson, A. Arbod, International Journal of Pharamaceutics, (1995) pp. 315-325, dated May 3, 1995.
"Correlation of rheological properties of an oil in water emulsion with manufacturing procedures and stability", by U.T. Lashmar and J. Beesley, International Journal of Pharamaceutics pp. 59-67, 1993.
U.S. Appl. No. 15/317,753 Office Action dated Jun. 8, 2018, 53 pages.

* cited by examiner

[Figure 1]
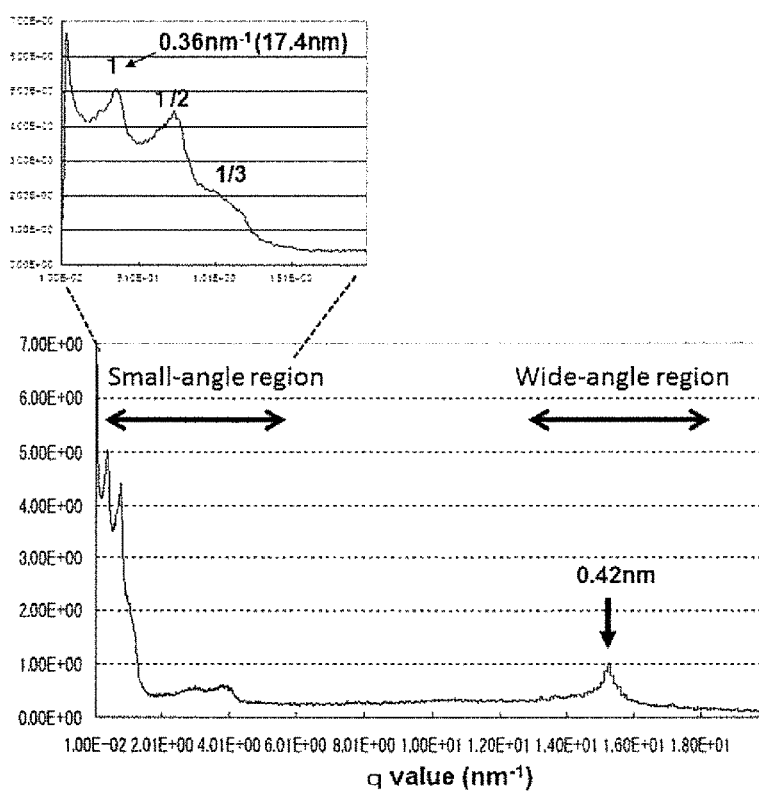
Fig.1 A mixture of behenyl alcohol:sodium N-stearoyl methyl taurine = 3:1 forms α-gel in water

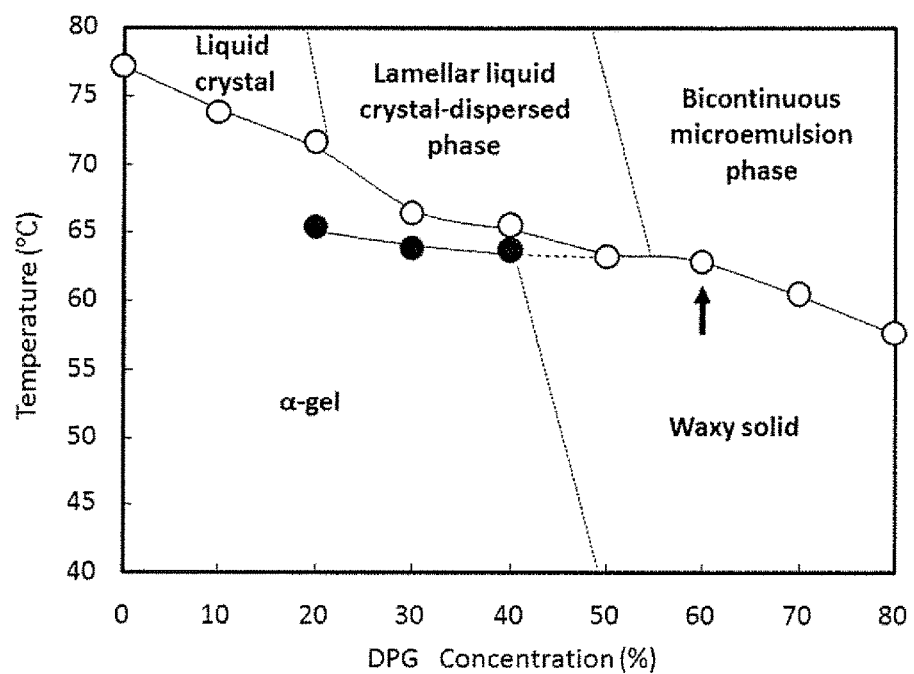
Fig.2 Phase states of a mixture of behenyl alcohol + sodium N-stearoyl methyl taurine / DPG / water

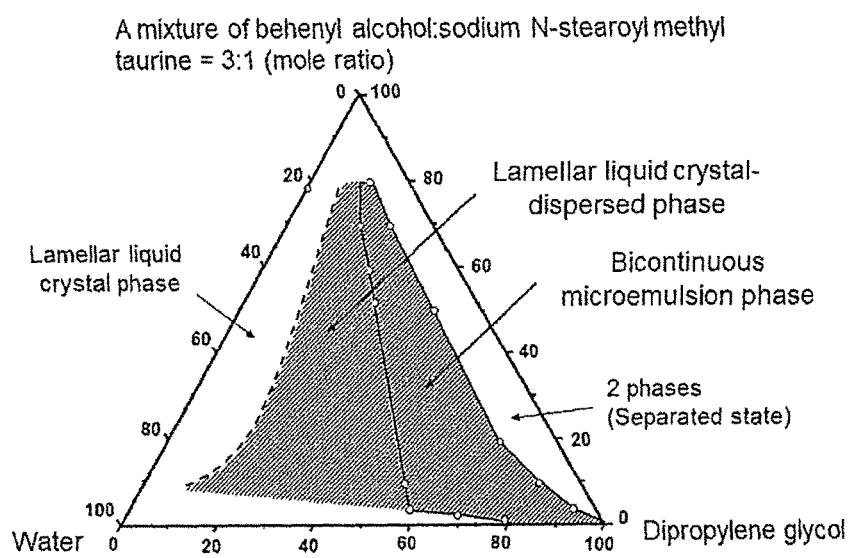
FIG. 3 Phase states of a mixture of behenyl alcohol + sodium N-stearoyl methyl taurine / DPG / water (80 °C)

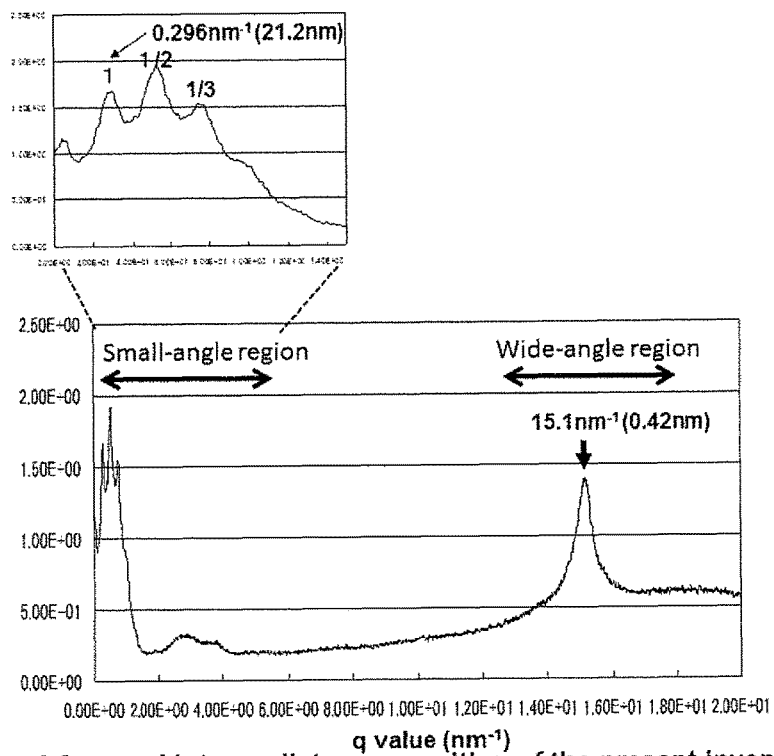
Fig. 4 An α-gel intermediate composition of the present invention generates α-gel by the addition of water

[Figure 5]
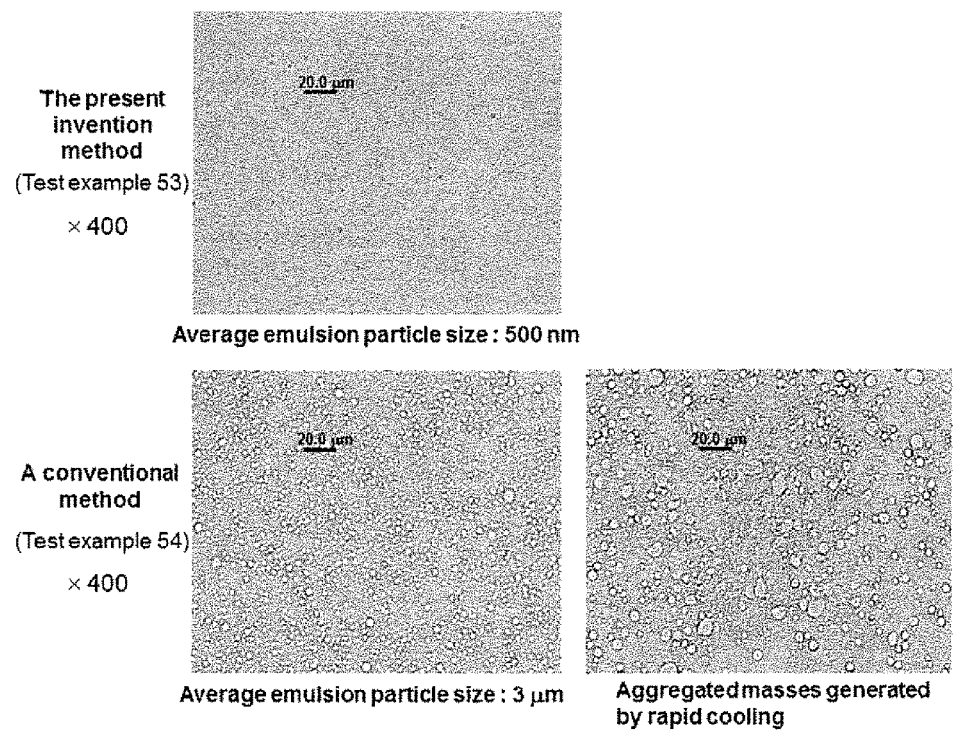
Fig.5 Emulsion particle size of the α-gel-containing O/W emulsion cosmetics prepared by two different production methods

α-GEL-INTERMEDIATE COMPOSITION, AND PRODUCTION METHOD FOR α-GEL-CONTAINING O/W EMULSION COSMETIC USING SAID COMPOSITION

RELATED APPLICATIONS

This application claims priority from Ser. No. PCT/JP2015/065435 filed May 28, 2015, the contents of which are incorporated by reference which claims the priority of Japanese Patent Application No. 2014-122250 filed on Jun. 13, 2014, which is incorporated herein by reference.

TECHNICAL FIELD

The present invention relates to an intermediate composition for the preparation of an α-gel-containing O/W emulsion cosmetic and a production method of the α-gel-containing O/W emulsion cosmetic by the use of the intermediate composition.

BACKGROUND ART

In the preparation of emulsion cosmetics, the stabilization of the emulsion is a very important issue; thus various technologies have been developed to improve the stability (for example, Non-Patent Literatures 1 and 2).

For example, in the case of O/W (=oil-in-water type) emulsions, if liquid crystal or α-gel layers are formed around emulsion particles, aggregation/coalescence of emulsion particles are physically suppressed; thus the stability is known to improve significantly (Non-Patent Literatures 1 and 2).

α-Gel is an aggregate consisting of lamellar bi-layers (bimolecular membranes) formed by a hydrophilic surfactant and a linear higher alcohol or non-neutralized fatty acid having 16 or more carbon atoms in the presence of water (Non-Patent Literature 3). The higher alcohol and surfactant are orderly arranged in the bi-layers with the molar ratio of 3:1 (specifically, the hydrophilic group of the higher alcohol is positioned at hexagonal corners, and the hydrophilic group of the surfactant is positioned at the hexagonal center) to form a hexagonal system (Non-Patent Literature 3, pages 81 to 82). It is structurally similar to lamellar liquid crystals; however, the packing of alkyl chains is higher than lamellar liquid crystals. Therefore, blocking property is high and also excellent in the water retention; thus the above-described stabilization technology in which α-gel is used is widely used in O/W emulsion cosmetics (for example, Patent Literature 1).

However, the O/W emulsion cosmetic containing α-gel in the external phase (in the present application, it is called an α-gel-containing O/W emulsion cosmetic) has low viscosity stability over time, and it is known that the viscosity increases over time (that is, the product gradually hardens).

In addition, the cooling process of the emulsion is not easy in the production process. If the cooling rate is very slow, a large amount of α-gel is formed in the external phase and the cosmetic is too hard. If cooling is too fast, crystals of higher alcohol deposit and aggregated mass is sometimes generated. Therefore, the process is normally carried out while the cooling rate is being adjusted with a cooling device (Onlator etc.). However, a large amount of energy is necessary; in addition, a large amount of waste water is generated in the washing process of cooling devices; thus the burden is heavy on cost and the environment.

Furthermore, in the conventional production method, the preparation of an emulsion with small emulsion particle sizes (specifically, the particle size of 1 μm or less) has been known to be difficult.

Concerning the emulsion particle size among the above-described problems that the α-gel-containing O/W emulsion cosmetics have, the present inventors have shown that an α-gel-containing O/W emulsion cosmetic having the emulsion particle size of 1 μm or less can be prepared by initially preparing a W/O emulsion and subsequently inverting it into an O/W emulsion (Patent Literature 2).

Concerning the above-described burden on cost and the environment, the reduction of the burden has been attempted by preparing a high-concentration intermediate composition. In Patent Literature 3, the present inventors have reported that a α-gel-containing O/W emulsion cosmetic can be prepared without using a cooling device by preparing a high-concentration emulsion portion by the emulsification, at 70° C. or higher, of an oil phase containing a higher alcohol having 16 or more carbon atoms and a nonionic surfactant, which together can form α-gel, an oil component, and only a portion of the aqueous phase and by diluting the high-concentration emulsion portion with the residual aqueous phase at around room temperature. Patent Literature 4 discloses a method to prepare an O/W emulsion cosmetic by preparing a fine oil gel (oil-gel emulsion portion) by adding a heated oil phase with stirring to an aqueous phase, where a high-concentration water-soluble solvent and a nonionic surfactant are dissolved by heating at around 70° C., and by subsequently dispersing the oil gel in the aqueous phase (in particular, refer to Example 3 of Patent Literature 4).

However, concerning the viscosity change over time, which is the biggest problem of the α-gel-containing O/W emulsion cosmetic, no effective means of its suppression have been reported. In addition, the above-described intermediate compositions (high-concentration emulsion portion and oil-gel emulsion portion) are in a thermodynamically non-equilibrated state; thus there has been a demand for a stably storable intermediate composition.

PRIOR ART DOCUMENTS

Patent Literatures

[Patent literature 1] Japanese Patent Publication No. 3829048
[Patent literature 2] Japanese Patent Publication No. 5047369
[Patent literature 3] Japanese Patent Publication No. 4709320
[Patent literature 4] Japanese Examined Patent Publication No. H02-51665

Non-Patent Literatures

[Non-Patent Literature 1] Yakugaku Zasshi, Vol. 104, No. 9, pages 986-989, 1894.
[Non-Patent Literature 2] Toshiyuki Suzuki, Journal of SCCJ, Vol. 44, No. 2, pages 103-117, 2010.
[Non-Patent Literature 3] "Physical Chemistry of Cetyl Alcohol", authored by Shoji Fukushima, published by Fragrance Journal Ltd., pages 79-83, 1992.
[Non-Patent Literature 4] "Latest Functional Creation/Material Development/Applied Technology for Cosmetics", authored by Masahiko Abe, Toshiyuki Suzuki, and Hiroshi Fukui, published by Gijutsu Kyoiku Shuppansha, 2007.

[Non-Patent Literature 5] "Systematic Organic Qualitative Analysis (Edition for Mixtures)", authored by Makoto Fujita and Masami Akatsuka, published by Kyoritsu Shuppan Co., Ltd., 1974.

SUMMARY OF INVENTION

Technical Problem

The present invention was made in view of the above-described problem of the conventional art, and an object is to provide a method to prepare, easily and steadily, an α-gel-containing O/W emulsion cosmetic, wherein the viscosity change is very little over time and the emulsion stability is excellent, without using a cooling device.

Solution to Problem

In order to achieve the above-described object, the present inventors focused on the conventional production method of α-gel-containing O/W emulsion cosmetics. As described above, in the conventional method, an α-gel-containing O/W emulsion cosmetic was prepared by carrying out the emulsification by adding with stirring the oil phase, where oil and a higher alcohol were dissolved by heating at around 70° C., to the aqueous phase, where a hydrophilic surfactant and other aqueous components were dissolved in water and heated at around 70° C., and by cooling with stirring the obtained emulsion to around 35° C. in a cooling device (for example, Patent Literatures 1-3). That is, it is a method to effectively form α-gel around the emulsion particles by dissolving, among the components of α-gel (a hydrophilic surfactant, a linear higher alcohol having 16 or more carbon atoms, and water), the hydrophilic surfactant into the aqueous phase and the lipophilic higher alcohol into the oil phase, respectively, and by allowing the leaching of the higher alcohol from the inside of the emulsion particle to the aqueous phase after emulsifying the two phases by mixing.

The dissolution of high-hydrophilicity components in the aqueous phase and the dissolution of high-lipophilicity components in the oil phase are very sensible means, and all of the Patent Literatures 1 to 4 followed this common sense. For obtaining emulsion particles covered with α-gel, the above-described production method, which is designed so that all the components of α-gel get together on the surface of emulsion particles, is very efficient and purposeful.

Thus, the present inventors decided to seek means to solve the above-described problems by defying common sense. Specifically, the present inventors investigated a possibility of the preparation of a liquid phase where α-gel is not formed, though all the components of α-gel are dissolved in it, but the formation of α-gel can be easily induced by a specific operation. In the present application, "liquid phase (namely, liquid-phase state)" and "liquid" are synonymous.

After trial and error, it was found that a mixture of an water-soluble solvent with the IOB value of 1.5 to 3.5 and water with the mass ratio of 5:5 to 8:2 becomes a low-viscosity liquid phase without α-gel in the range of 65 to 85° C., even when a higher alcohol having 16 or more carbon atoms and an anionic surfactant has been dissolved in it with the mixing ratio (3:2 to 5:1), where α-gel can be easily formed. The low-viscosity liquid phase consisted of a bicontinuous microemulsion phase or a lamellar liquid crystal-dispersed bicontinuous microemulsion phase, and the formation of α-gel was easily induced by adding water at around room temperature to the liquid phase and mixing. When oil at 85° C. or lower and water at around room temperature were sequentially added to the low-viscosity liquid phase and mixed, it was found that an α-gel-containing O/W emulsion having a very high viscosity stability over time and excellent in emulsion stability can be obtained, thus leading to the completion of the present invention.

Furthermore, it was also found that the above-described low-viscosity liquid phase becomes a waxy solid at room temperature and it can be stably stored in that state over a long period.

That is, the present invention provides an α-gel intermediate composition consisting of:
(A) 20 to 80 mass % of a mixture containing one or more higher alcohols having 16 or more carbon atoms and an anionic surfactant in the mole ratio of 3:2 to 5:1, and
(B) 20 to 80 mass % of a mixture containing one or more water-soluble solvents having the IOB value of 1.5 to 3.5 and water in the mass ratio of 5:5 to 8:2,
and the composition is a liquid consisting of a bicontinuous microemulsion phase or a lamellar liquid crystal-dispersed bicontinuous microemulsion phase at 65 to 85° C. and a solid at room temperature.

As the anionic surfactant of the above-described (A), one or more surfactants selected from the group consisting of N-acyl methyl taurine salts, N-acyl glutamic acid salts, and monoalkylphosphoric acid salts can preferably be used.

Furthermore, as the water-soluble solvent having the IOB value of 1.5 to 3.5 of the above-described (B), one or more water-soluble solvents selected from the group consisting of dipropylene glycol, isoprene glycol, 1,3-butanediol, polyethylene glycol, and propylene glycol can preferably be used.

In addition, the present invention provides a production method of an α-gel-containing O/W emulsion cosmetic, wherein the production method comprises the below-described processes (i) to (iii);
(i) a process to obtain an α-gel intermediate composition consisting of a bicontinuous microemulsion phase or a lamellar liquid crystal-dispersed bicontinuous microemulsion phase by mixing with stirring the below-described components (A) and (B) at 65 to 85° C.,
(A) 20 to 80 mass % of a mixture containing one or more higher alcohols having 16 or more carbon atoms and an anionic surfactant in the mole ratio of 3:2 to 5:1, and
(B) 20 to 80 mass % of a mixture containing one or more water-soluble solvents having the IOB value of 1.5 to 3.5 and water in the mass ratio of 5:5 to 8:2,
(ii) a process to add oil that is 85° C. or lower to the α-gel intermediate composition obtained in process (i) while stirring the composition at 65 to 85° C., and
(iii) a process to add water that is 30° C. or lower and 3 to 50 times by mass, of the mixture, to the mixture of the α-gel intermediate composition and oil obtained in process (ii) while stirring the mixture.

The above-described process (ii) can be carried out after the storage, at room temperature, of the α-gel intermediate composition obtained in the above-described process (i).

Advantageous Effects of Invention

The present invention provides an intermediate composition to easily and steadily prepare an α-gel-containing O/W emulsion cosmetic having a very high viscosity stability over time and excellent in emulsion stability without using a cooling device, which has heavy burden on cost and the environment, and a production method of the α-gel-containing O/W emulsion cosmetic with the use of the intermediate composition. The α-gel intermediate composition of the present invention easily generates α-gel by the addition of water after a low-viscosity liquid phase is formed by heating to 65 to 85° C. Therefore, an α-gel-containing O/W emulsion can be easily and steadily obtained by adding heated oil to the low-viscosity liquid phase and subsequent addition of water at around room temperature (or water wherein aqueous components are dissolved) and mixing. Furthermore, the α-gel intermediate composition of the present invention can be stably stored at room temperature over a long period.

BRIEF DESCRIPTION OF DRAWINGS

FIG. 1 shows the results of X-ray diffraction for the composition where water was added to a mixture of behenyl alcohol:sodium N-stearoyl methyl taurine=3:1 (mole ratio) and mixed with stirring at 80° C.

FIG. 2 shows the phase states that the composition containing 30 mass % of the mixture of behenyl alcohol: sodium N-stearoyl methyl taurine=3:1 (mole ratio) and 70 mass % of the mixture of dipropylene glycol/water (mass ratio is plotted on the ordinate) can take at various temperatures.

FIG. 3 shows the phase states that the composition consisting of the mixture of behenyl alcohol:sodium N-stearoyl methyl taurine=3:1 (mole ratio), dipropylene glycol, and water can take at 80° C.

FIG. 4 shows the results of X-ray diffraction after the α-gel intermediate composition of Test Example 31 of the present application was stored at room temperature for a few weeks and then heated to 80° C., room-temperature water that is 8 times by mass of the intermediate composition was added, and they were mixed with stirring.

FIG. 5 shows optical micrographs of the α-gel-containing O/W emulsion cosmetics prepared by two different production methods even though the formulations are the same (production method of the present invention: Test Example 53 in the present application; conventional production method: Test Example 54 in the present application).

DESCRIPTION OF EMBODIMENTS

Hereinafter, preferable embodiments of the present invention will be explained. At first, the α-gel intermediate composition of the present invention and the components thereof will be explained in detail.

PEG, POE, and POP in the following description are abbreviations for polyethylene glycol, polyoxyethylene, and polyoxypropylene, and the numbers after the hyphen in the abbreviations represent the respective average addition mole numbers. DPG is an abbreviation for dipropylene glycol.

α-Gel Intermediate Composition

The α-gel intermediate composition of the present invention is a composition containing
(A) a mixture containing one or more higher alcohols having 16 or more carbon atoms and an anionic surfactant in the mole ratio of 3:2 to 5:1, and
(B) a mixture containing one or more water-soluble solvents with the IOB value of 1.5 to 3.5 and water in the mass ratio of 5:5 to 8:2,
with the mass ratio of (A):(B)=20:80 to 80:20, it is a low-viscosity liquid consisting of a bicontinuous microemulsion phase or a lamellar liquid crystal-dispersed bicontinuous microemulsion phase (hereinafter, called "a lamellar liquid crystal-dispersed phase" in the present application) at 65 to 85° C., and it becomes a waxy solid at room temperature. In the above-described solid state, the long-term storage is possible at room temperature.

Here, the term "IOB value (inorganic organic balance)" means the ratio of inorganic value and organic value calculated by the organic conception diagram of Makoto Fujita, and it is an indicator of the polarity of organic compounds (Non-Patent Literature 5). The higher the IOB value of an organic compound, the higher the polarity of the compound.

The α-gel intermediate composition of the present invention can easily generate an O/W emulsion cosmetic in which the surrounding of the oil phase (namely, emulsion particles) is covered with α-gel, when the composition has been heated to 65 to 85° C. and then oil at 85° C. or lower and water at 30° C. or lower are sequentially added to the composition with mixing. Therefore, the α-gel intermediate composition of the present invention can be used as an intermediate composition for α-gel-containing O/W emulsion cosmetics.

"α-Gel" in the present invention means an aggregate consisting of lamellar bi-layers, where the hexagonal system is the basic unit, which is formed of a linear higher alcohol having 16 or more carbon atoms and an anionic surfactant in the molar ratio of 3:1 (refer to Non-Patent Literature 3, pages 81 to 82). In the X-ray diffraction, α-gel shows sharp peaks corresponding to the long spacing of the order of several tens to several hundred Å in the small-angle region, where the diffraction angle is about 10° or lower, and a sharp single peak (in the vicinity of 4.15 Å) corresponding to the hexagon of the hexagonal system (namely, short spacing) in the wide-angle region, where the diffraction angle is about 10° or more. When compared with lamellar liquid crystals, it is difficult to distinguish α-Gel from lamellar liquid crystals by the patterns in the small-angle region. However, the patterns in the wide-angle region is clearly different each other (in the case of lamellar liquid crystals, a halo, namely a broad single peak is obtained in the vicinity of 4.5 Å); thus both can easily be distinguished (refer to Non-Patent Literature 4, pages 238-241).

Accordingly, in the present application, when multiple peaks corresponding to the long spacing are obtained in the small-angle region of the X-ray diffraction and a sharp single peak is obtained in the wide-angle region, it is determined to be an α-gel-containing composition.

The "bicontinuous microemulsion phase", which can be formed from the α-gel intermediate composition of the present invention at 65 to 85° C., is a liquid phase of thermodynamically equilibrated one-phase state consisting of repeated bi-layers formed of a higher alcohol having 16 or more carbon atoms and an anionic surfactant oriented so that the respective hydrophilic groups (or lipophilic groups) are in close proximity. Unlike the above-described α-gel, there is no regularity in the arrangement of the higher alcohol and the anionic surfactant along the direction of membrane plane of the above-described repeated bi-layers, and the system as a whole shows optical isotropy. It becomes colorless and transparent at around 80° C.; when hydrophilic dye/hydrophobic dye are added, the diffusion of both dyes to the entire system is observed; thus it can easily be confirmed that this is a bicontinuous phase.

The "lamellar liquid crystal-dispersed phase", which can be formed from the α-gel intermediate composition of the present invention at 65 to 85° C. is a liquid phase in which lamellar liquid crystals are dispersed in the above-described "bicontinuous microemulsion phase" as a result of local liquid crystallization of the repeated bi-layers. Similarly to the above-described "bicontinuous microemulsion phase", it becomes colorless and transparent at around 80° C., and the diffusion of hydrophilic and hydrophobic dyes to the entire system can be observed. However, the phase contains lamellar liquid crystals; therefore, it shows optical anisotropy.

Accordingly, when a composition consisting of a lamellar liquid crystal-dispersed phase is centrifuged at a low speed (for example, low-speed centrifugation at about 2000 rpm with a himacCF7D2-type centrifuge manufactured by Hitachi Koki Co., Ltd.), the separation into the optically isotropic upper layer (bicontinuous microemulsion phase) and the optically anisotropic lower layer (the phase in which lamellar liquid crystals are concentrated) takes place; thus it can be easily distinguished from the bicontinuous microemulsion phase. In the present application, the phase in which the percentage of the lower layer is about 5 volume % or lower with respect to the total composition was defined to be a "lamellar liquid crystal-dispersed phase".

In the present application, the liquid phase (liquid) consisting of the above-described bicontinuous microemulsion phase and lamellar liquid crystal-dispersed phase is sometimes called "low-viscosity liquid phase (liquid)". The term "low-viscosity" is used in contradistinction to that the viscosities of α-gel and a lamellar liquid crystal phase are very high (close to a solid).

Higher Alcohols Having 16 or More Carbon Atoms

Higher alcohols having 16 or more carbon atoms and usable as component (A) of the present invention are not limited in particular so far as they can form α-gel in water with an anionic surfactant and usable in the fields of cosmetics, pharmaceuticals, and quasi-drugs. Specific examples include cetyl alcohol, cetostearyl alcohol, stearyl alcohol, behenyl alcohol, and butyl alcohol. They are preferably linear higher alcohols having 16 to 24 carbon atoms, and more preferably linear saturated higher alcohols having 16 to 24 carbon atoms. The higher alcohols of the present application include glycerin mono-fatty acid esters.

In the present invention, one or more higher alcohols having 16 or more carbon atoms can be used as component (A).

Anionic Surfactants

The anionic surfactant usable as component (A) of the present invention is preferably one or more surfactants selected from the group consisting of N-acyl methyl taurine salts, N-acyl glutamic acid salts, and monoalkylphosphoric acid salts. Examples of N-acyl methyl taurine salts include coconut oil fatty acid methyl taurine salt, N-caproyl methyl taurine salt, N-lauroyl methyl taurine salt, N-myristoyl methyl taurine salt, N-palmitoyl methyl taurine salt, N-stearoyl methyl taurine salt, and N-oleoyl methyl taurine salt. As the preferable counter ion, sodium, potassium, triethanolamine, ammonia, etc. can be listed. Among them, N-stearoyl methyl taurine salt is preferable in the present invention, and the most preferable is sodium N-stearoyl methyl taurine.

Examples of N-acyl glutamic acid salts include N-cocoyl glutamic acid salt, N-lauroyl glutamic acid salt, N-myristoyl glutamic acid salt, N-palmitoyl glutamic acid salt, N-stearoyl glutamic acid salt, and N-oleoyl glutamic acid salt; as the preferable counter ion, sodium, potassium, triethanolamine, etc. can be listed. Among them, N-stearoyl glutamic acid salt is preferable in the present invention, and the most preferable is sodium N-stearoyl glutamate.

Examples of monoalkylphosphoric acid salts include laurylphosphoric acid salt, myristylphosphoric acid salt, palmitylphosphoric acid salt, stearylphosphoric acid salt; as the preferable counter ion, sodium, potassium, etc. can be listed. Among them, stearylphosphoric acid salt is preferable in the present invention, and sodium stearylphosphate is most preferable.

The mole ratio of a higher alcohol having 16 or more carbon atoms and an anionic surfactant, which are blended as component (A) of the present invention, is preferably 3:2 to 5:1 and most preferably 3:1. That is because when the mole ratio of the above-described higher alcohol and the anionic surfactant is within the range of 3:2 to 5:1, α-gel is known to be effectively formed.

When the rate of the anionic surfactant is higher than the above-described mole ratio, α-gel may not be sufficiently formed on the surrounding of oil droplets of the O/W emulsion cosmetic, and when the rate of the higher alcohol is higher, crystals of the higher alcohol may be generated in the emulsion cosmetic.

Water-Soluable Solvents with the IOB Value of 1.5 to 3.5

The water-soluble solvents with the IOB value of 1.5 to 3.5, usable as component (B) in the present invention, are not limited in particular so far as they are commonly used in cosmetics. However, one or more water-soluble solvents selected from the group consisting of dipropylene glycol (IOB=1.80), isoprene glycol (IOB=2.20), 1,3-butanediol (IOB=2.50), 1,4-butanediol (IOB=2.50), polyethylene glycol having the average molecular weight of 300 or lower (for example, PEG-200 with IOB=2.92), and propylene glycol (IOB=3.33) are preferable. Among them, dipropylene glycol, isoprene glycol, 1,3-butanediol, PEG-200, and propylene glycol are more preferable, and dipropylene glycol, 1,3-butanediol, and propylene glycol are most preferable.

In the present invention, one or more water-soluble solvents with the IOB value of 1.5 to 3.5 can be used as component (B).

In the α-gel intermediate composition of the present invention, the blending ratio of the above-described component (A) and component (B) is preferably (A):(B)=20:80 to 80:20 in the mass ratio. If (A) is less than 20 mass %, the feeling in use of the O/W emulsion cosmetic tends to be poor. If (A) is more than 80 mass %, a bicontinuous microemulsion phase or a lamellar liquid crystal-dispersed phase may not be formed.

In the following, oil and water blendable in the α-gel-containing O/W emulsion cosmetic of the present invention will be explained. These are the components that become the internal phase and the external phase of the α-gel-containing O/W emulsion cosmetic of the present invention after adding them to the above-described α-gel intermediate composition.

Oil

In the present invention, the oil blendable as the inner layer of the α-gel-containing O/W emulsion cosmetic is not limited in particular. Examples include liquid oils and fats, solid oils and fats, waxes, hydrocarbon oils, higher fatty acids, synthetic ester oils, silicone oils, and some higher alcohols (includes those usable as component (A) in the present application). The blending quantity of the oil is not limited in particular; however, it is preferable to be 1 to 50 mass % with respect to the α-gel-containing O/W emulsion cosmetic. Outside of the range, the feeling in use may become poor.

Examples of liquid oils and fats include avocado oil, *camellia* oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cotton seed oil, *perilla* oil, soybean oil, peanut oil, tea seed oil, kaya oil, rice bran oil, china *paulownia* oil, Japanese *paulownia* oil, jojoba oil, germ oil, and triglycerin.

Examples of solid oils and fats include cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, beef leg tallow, Japan wax, and hydrogenated castor oil.

Examples of waxes include beeswax, candelilla wax, cotton wax, carnauba wax, bayberry wax, ibota wax, whale wax, montan wax, rice bran wax, lanolin, kapok wax, acetylated lanolin, liquid lanolin, sugarcane wax, isopropyl lanolin fatty acid, hexyl laurate, hydrogenated lanolin, jojoba wax, hard lanolin, shellac wax, POE lanolin alcohol ether, POE lanolin alcohol acetate, POE cholesterol ether, lanolin fatty acid polyethylene glycol, POE hydrogenated lanolin alcohol ether, and cetyl palmitate.

Example of hydrocarbon oils include liquid paraffin, ozokerite, squalane, pristane, paraffin, ceresin, squalene, petrolatum, and microcrystalline wax.

Examples of higher fatty acids include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA).

Examples of synthetic ester oils include cetyl octanoate, myristyl myristate, glyceryl tri-2-ethylhexanoate, pentaerythritol tetra-2-ethylhexanoate, dioctyl succinate, and tripropylene glycol dineopentanoate.

Examples of silicone oils include linear polysiloxanes (for example, dimethylpolysiloxane, methylphenylpolysiloxane, diphenylpolysiloxane, etc.); cyclic polysiloxanes (for example, octamethylcyclotetrasiloxane, decamethylcyclopentasiloxane, dodecamethylcyclohexasiloxane, etc.), silicone resins with a three-dimensional network, silicone rubbers, various modified polysiloxanes (amino-modified polysiloxane, polyether-modified polysiloxane, alkyl-modified polysiloxane, fluorine-modified polysiloxane, etc.), and acrylsilicones.

Water

In the present invention, water that can be added to the α-gel intermediate composition, as the external phase of the α-gel-containing O/W emulsion cosmetic, is preferably water near room temperature. The upper-limit temperature is about 30° C., and the lower-limit temperature is about 15° C. In the present invention, "room temperature" means 15-30° C.

In addition, water-soluble components among the below-illustrated optional components can be suitably blended into the water within the range that the effect of the present invention is not impaired.

Optional Components

In the α-gel-containing O/W emulsion cosmetic of the present invention, in addition to the above-described essential components, components normally used in cosmetics, pharmaceuticals, etc. can be blended within the range that the stability thereof is not affected. Examples of such optional components include powder components, amphoteric surfactants, nonionic surfactants, moisturizers, thickeners, film-forming agents, UV absorbers, metal ion sequestering agents, pH adjusters, skin nutrients, vitamins, antioxidants, antioxidant promoters, and perfumes. These optional components can be suitably blended by dissolving oil-soluble components in the above-described oil that is heated to 85° C. or lower and water-soluble components in the above-described water at 30° C. or lower, respectively. As the optional components, compounds identical to the above-described component (B) can be used.

Examples of powder components include inorganic powders (for example, talc, kaolin, mica, sericite, muscovite, phlogopite, synthetic mica, lepidolite, biotite, vermiculite, bentonite, hectorite, laponite, magnesium carbonate, calcium carbonate, aluminum silicate, barium silicate, calcium silicate, magnesium silicate, strontium silicate, tungstic acid metal salts, magnesium, silica, zeolite, barium sulfate, calcined calcium sulfate (calcined gypsum), calcium phosphate, fluorapatite, hydroxyapatite, ceramic powder, metal soaps (for example, zinc myristate, calcium palmitate, aluminum stearate), boron nitride, etc.); organic powders (for example, polyamide resin powder (nylon powder), polyethylene powder, poly(methyl methacrylate) powder, polystyrene powder, styrene-acrylic acid copolymer resin powder, benzoguanamine resin powder, polytetrafluoroethylene powder, cellulose powder, etc.); inorganic white pigments (for example, titanium dioxide, zinc oxide, etc.); inorganic red pigments (for example, iron oxide (bengala), iron titanate, etc.); inorganic brown pigments (for example, γ-iron oxide etc.); inorganic yellow pigments (for example, yellow iron oxide, yellow ocher, etc.); inorganic black pigments (for example, black iron oxide, low-order titanium oxide, etc.); inorganic violet pigments (for example, mango violet, cobalt violet, etc.); inorganic green pigments (for example, chromium oxide, chromium hydroxide, cobalt titanate, etc.); inorganic blue pigments (for example, ultramarine, Prussian blue, etc.); pearl pigments (for example, titanium oxide-coated mica, titanium oxide-coated bismuth oxychloride, titanium oxide-coated talc, colored titanium oxide-coated mica, bismuth oxychloride, fish scale flake, etc.); metal powder pigments (for example, aluminum powder, copper powder, etc.); organic pigments such as zirconium, barium, or aluminum lakes (for example, organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404; and Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, Blue No. 1, etc.); and natural dyes (for example, chlorophyll, j-carotene, etc.).

Examples of amphoteric surfactants include imidazoline-type amphoteric surfactants (for example, sodium 2-undecyl-N,N,N-(hydroxyethylcarboxymethyl)-2-imidazoline, 2-cocoyl-2-imidazolinium hydroxide-1-carboxyethyloxy disodium salt, etc.); and betaine-type surfactants (for example, 2-heptadecyl-N-carboxymethyl-N-hydroxyethyl-imidazolinium betaine, lauryl dimethylamino acetic acid betaine, alkylbetaines, amidobetaines, sulfobetaines, etc.).

Examples of lipophilic nonionic surfactants include sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, penta-2-ethylhexyl acid diglycerol sorbitan, tetra-2-ethylhexyl acid diglycerol sorbitan, etc.); glycerin polyglycerin fatty acids (for example, glycerin monocottonseed oil fatty acid, glyceryl monoerucate, glyceryl sesquioleate, glyceryl monostearate, glycerin α,α'-oleic acid pyroglutamic acid, monostearate glycerin malic acid, etc.); propylene glycol fatty acid esters (for example, monostearate propylene glycol, etc.); hydrogenated castor oil derivatives; and glycerin alkyl ethers.

Examples of hydrophilic nonionic surfactants include POE-sorbitan fatty acid esters (for example, POE-sorbitan monooleate, POE-sorbitan monostearate, POE-sorbitan monooleate, POE-sorbitan tetraoleate, etc.); POE sorbit fatty acid esters (for example, POE-sorbit monolaurate, POE-sorbit monooleate, POE-sorbit pentaoleate, POE-sorbit monostearate, etc.); POE-glycerin fatty acid esters (for example, POE-glycerin monostearate, POE-glycerin monoisostearate, POE-glycerin triisostearate, etc.); POE-fatty acid esters (for example, POE-distearate, POE-monodioleate, ethylene glycol distearate, etc.); POE-alkyl ethers (for example, POE-lauryl ether, POE-oleyl ether, POE-stearyl ether, POE-behenyl ether, POE-2-octyldodecyl ether, POE-cholestanol ether, etc.); Pluronic types (for example, Pluronic etc.); POE/POP-alkyl ethers (for example, POE/POP-cetyl ether, POE/POP-2-decyltetradecyl ether, POE/POP-monobutyl ether, POE/POP-hydrogenated lanolin, POE/POP-glycerin ether, etc.); tetraPOE/tetraPOP-ethylenediamine condensation products (for example, Tetronic etc.); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, POE-hydrogenated castor oil maleic acid, etc.); POE-beeswax/lanolin derivatives (for example, POE-sorbit beeswax etc.); alkanolamide (for example, coconut oil fatty acid diethanolamide, lauric acid monoethanolamide, fatty acid isopropanolamide, etc.); POE-propylene glycol fatty acid ester, POE-alkylamine; POE-fatty acid amide; sucrose fatty acid esters; alkylethoxydimethylamine oxide; and trioleyl phosphate.

In addition, as a thickener, natural/semisynthetic/synthetic polymer compounds can be blended.

Examples of natural water-soluble polymers include plant polymers (for example, gum arabic, tragacanth gum, galactan, guar gum, carob gum, karaya gum, locust bean gum, tamarind gum, carrageenan, pectin, agar, quince seed (marmelo), algecolloid (brown algae extract), starch (rice, corn, potato, wheat), glycyrrhizic acid); microbial polymers (for example, xanthan gum, dextran, succinoglucan, pullulan, etc.); and animal polymers (for example, collagen, casein, albumin, gelatin, etc.).

Examples of semisynthetic water-soluble polymers include starch polymers (for example, carboxymethyl starch, methylhydroxypropyl starch, etc.); cellulose polymers (methylcellulose, ethylcellulose, methylhydroxypropylcellulose, hydroxyethylcellulose, sodium cellulose sulfate, dialkyldimethylammonium sulfate cellulose, hydroxypropylcellulose, carboxymethylcellulose, sodium carboxymethylcellulose, crystalline cellulose, cellulose powder and hydrophobically modified compounds <example: partially stearoxy-modified> of these polymers and cation-modified compounds of these polymers, etc.); alginic acid polymers (for example, sodium alginate, alginic acid propylene glycol ester, etc.); and sodium pectate.

Examples of synthetic water-soluble polymers include vinyl polymers (for example, polyvinyl alcohol, polyvinylmethyl ether, polyvinylpyrrolidone, carboxyvinylpolymer, etc.); polyoxyethylene polymers (for example, polyoxyethylene-polyoxypropylene copolymers of polyethylene glycol 20,000, 40,000, or 60,000, etc.); poly(dimethyldiallylammonium halide)-type cationic polymers (for example, Merquat 100, manufactured by US Merck & Co.); copolymer-type cationic polymers of dimethyldiallylammonium halide and acrylamide (for example, Merquat 550 manufactured by US Merck & Co.); acrylic polymers (for example, sodium polyacrylate, polyethylacrylate, polyacrylamide, etc.); polyethyleneimine; cation polymers; and AlMg silicate (Veegum).

Examples of UV absorbers include benzoic acid-based UV absorber (for example, para-aminobenzoic acid (hereinafter, abbreviated as PABA), PABA monoglycerin ester, N,N-dipropoxyPABA ethyl ester, N,N-diethoxyPABA ethyl ester, N,N-dimethylPABA ethyl ester, N,N-dimethylPABA butyl ester, N,N-dimethylPABA ethyl ester, etc.); anthranilic acid UV absorber (for example, homomenthyl N-acetylanthranilate etc.); salicylic acid UV absorber (for example, amyl salicylate, menthyl salicylate, homomenthyl salicylate, octyl salicylate, phenyl salicylate, benzyl salicylate, p-isopropanolphenyl salicylate, etc.); cinnamic acid UV absorber (for example, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxycinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, etc.); benzophenone-type UV absorbers (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl-4'-phenyl-benzophenone-2-carboxylate, 2-hydroxy-4-N-octoxybenzophenone, 4-hydroxy-3-carboxybenzophenone, etc.); 3-(4'-methylbenzylidene)-d,l-camphor, 3-benzylidene-d,l-camphor; 2-phenyl-5-methylbenzoxazole; 2,2'-hydroxy-5-methylphenylbenzotriazole; 2-(2'-hydroxy-5'-t-octylphenyl) benzotriazole; 2-(2'-hydroxy-5'-methylphenylbenzotriazole; dianisoylmethane; 4-methoxy-4'-t-butyldibenzoylmethane; 5-(3,3-dimethyl-2-norbornylidene)-3-pentane-2-on, etc.); triazine-type UV absorbers (for example, 2-4[(2-hydroxy-3-dodecyloxypropyl)oxy]-2-hydroxyphenyl)-4,6-bis(2,4-dimethylphenyl)-1,3,5-triazine, 2-4[(2-hydroxy-3-tridecyloxypropyl)oxy]-2-hydroxyphenyl)-4,6-bis(2,4-dimethylphenyl)-1,3,5-triazine, etc.).

Examples of metal ion sequestering agents include 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

Examples of pH adjusters include buffers such as lactic acid-sodium lactate, citric acid-sodium citrate, and succinic acid-sodium succinate.

Examples of vitamins include vitamins A, B1, B2, B6, C, E, and derivatives thereof, pantothenic acid and derivatives thereof, and biotin.

Examples of antioxidants include tocopherols, dibutylhydroxytoluene, butylhydroxyanisole, and gallic acid esters.

Examples of antioxidant promoters include phosphoric acid, citric acid, ascorbic acid, maleic acid, malonic acid, succinic acid, fumaric acid, cephalin, hexametaphosphate, phytic acid, and ethylenediaminetetraacetic acid.

Examples of other blendable components include preservatives (ethyl paraben, butyl paraben, 1,2-alkanediol, phenoxyethanol, methylchloroisothiazolinone, etc.); anti-inflammatory agents (for example, glycyrrhizic acid derivatives, glycyrrhetinic acid derivatives, salicylic acid derivatives, hinokitiol, zinc oxide, allantoin, etc.); whitening agent (for example, saxifraga extract, arbutin, etc.); various extracts (for example, phellodendron bark, coptis rhizome, lithospermum root, peony root, swertia herb, birch, sage, loquat, *ginseng*, aloe, mallow, iris, grape, *coix* seed, luffa, lily, saffron, cnidium rhizome, ginger, *hypericum*, ononis, garlic, *capsicum*, citrus unshiu peel, *Angelica acutiloba*, seaweed, etc.), activators (for example, royal jelly, photosensitive elements, cholesterol derivatives, etc.); blood circulation promoters (for example, 4-hydroxy-3-methoxybenzyl nonylic acid amide, nicotinic acid benzyl ester, nicotinic acid β-butoxyethyl ester, capsaicin, zingerone, cantharides tincture, ichthammol, tannic acid, α-borneol, tocopherol nicotinate, inositol hexanicotinate, cyclandelate, cinnarizine, tolazoline, acetylcholine, verapamil, cepharanthine, γ-oryzanol, etc.); antiseborrheic agents (for example, sulfur, thianthol, etc.); anti-inflammatory agents (for example, tranexamic acid, thiotaurine, hypotaurine, etc.); aromatic alcohols (benzyl alcohol, benzyloxy ethanol, etc.).

In addition, others such as perfumes and exfoliating agents can be suitably blended within the range that the stability is not impaired.

The α-gel-containing O/W emulsion cosmetics of the present invention can be applied, for example, to the body such as skin and hair, and they can be used for skin cosmetics, hair cleanser, skin cleanser, styling agents, etc.

In the following, the production method of an α-gel-containing O/W emulsion cosmetic, in which the α-gel intermediate composition of the present invention is used, is explained.

Production Method of an α-Gel-Containing O/W Emulsion Cosmetic

The above-described α-gel intermediate composition is heated to 65 to 85° C., and a low-viscosity liquid phase consisting of a bicontinuous microemulsion phase or a lamellar liquid crystal-dispersed phase is obtained. While stirring the liquid phase, oil that is heated to 85° C. or lower is added. An α-gel-containing O/W emulsion cosmetic can be obtained by subsequently carrying out emulsification at room temperature by gradually adding water at 30° C. or lower and continuing stirring until room temperature is reached.

A special device is not necessary in the production process, and a stirring device normally used for the preparation of O/W emulsion cosmetics can be used for the above-described stirring. In addition, the temperature of the composition appropriately decreases by adding water at 30° C. or lower; thus cooling with a cooling device is not necessary. The suitable amount of added water at 30° C. or lower is about 3 to 50 times by mass with respect to the α-gel intermediate composition, and preferably about 5 to 25 times by mass.

EXAMPLES

Hereinafter, the present invention will be explained in further detail with reference to examples. However, the scope of the present invention is not limited by these examples. The blending quantities in the present examples are expressed in mass % unless otherwise noted.

Example 1: Preparation of Liquid Phase Wherein α-Gel Components are Dissolved without Forming α-Gel A mixture of behenyl alcohol ($CH_3(CH_2)_{21}OH$, average molecular weight: 306.96) and sodium N-stearoyl methyl taurine (molecular weight: 427.97) in the mole ratio of 3:1 is known to easily form α-gel in the presence of water. FIG. 1 shows the results of X-ray diffraction performed at room temperature (25° C.) after water was added to the mixture and mixed at 80° C. by stirring. In the small-angle region, multiple peaks corresponding to the long spacing were detected; in the wide-angle region, a sharp single peak corresponding to the short spacing of about 0.42 nm was detected; thus it is understood that α-gel is formed.

Then, various materials were added to the water that dissolves the above-described mixture, and the effect thereof on the formation of α-gel was investigated. When dipropylene glycol was added, the formation of α-gel was effectively suppressed and a low-viscosity liquid phase without α-gel could be obtained. The details are explained below.

Test Composition 1 of the below-described formulation was prepared according to the below-described preparation method, and the temperatures of phase transition/melting were analyzed by carrying out differential scanning calorimetry. The results are shown in FIG. 2; white circles represent temperatures at which an endothermic or exothermic peak was observed and black circles represent temperatures at which a shoulder peak was observed. According to the below-described criteria, the determination of the phase state under the respective conditions was also carried out.

<Formulation/Method of Preparation for Test Composition 1>

The below-described (A) (30 mass %) and (B) (70 mass %) were mixed; it was heated to 80° C. and mixed with stirring.

(A) Behenyl alcohol:sodium N-stearoyl methyl taurine=3:1 (mole ratio) mixture
(B) Mixture of dipropylene glycol:water=1:0 to 0:1 (mass ratio)

<Determination of Phase State>

For the solid, polarizing microscope observation and/or X-ray diffraction was carried out except for the compositions visually determined as a waxy solid (indicated as "W-state solid" in the table), and the presence or absence of liquid crystals and α-gel was determined.

For the liquid phase, the presence or absence of phase separation was visually determined. For the composition without phase separation, the following determination was carried out.

Bicontinuous Microemulsion Phase

If both dyes diffused over the entire composition, when hydrophilic dye and hydrophobic dye were added, and optical anisotropy was not observed under crossed nicols of polarizing microscope observation, the phase was determined as a "bicontinuous microemulsion phase".

Liquid Phase Containing a Lamellar Liquid Crystal-Dispersed Phase, a Lamellar Liquid Crystal Phase, and α-Gel If both dyes diffused over the entire composition, when hydrophilic dye and hydrophobic dye were added, and optical anisotropy was observed under crossed nicols of polarizing microscope observation, the composition was further centrifuged at a low speed (low-speed centrifugation at about 2000 rpm with a himacCF7D2-type centrifuge manufactured by Hitachi Koki Co., Ltd.), and the upper layer, which does not show optical anisotropy, and the lower layer, which shows optical anisotropy were separated. X-ray diffraction was carried out for the lower layer, and the presence or absence of liquid crystals and/or α-gel was determined. When the lower layer consists of mainly lamellar liquid crystals and the percentage of the lower layer is about 5 volume % or lower of the total composition, the phase was determined to be a "lamellar liquid crystal-dispersed phase", and when the percentage of the lower layer is higher than about 5 volume %, the phase was determined as a "lamellar liquid crystal phase". If the lower layer mainly comprises α-gel, it was determined as a "liquid phase containing α-gel".

FIG. 2 shows that a mixture containing behenyl alcohol and sodium N-stearoyl methyl taurine in the mole ratio of 3:1 forms α-gel, when dissolved in water, under the wide temperature conditions of about 40 to 72° C., and it becomes a lamellar liquid crystal phase at a higher temperature than about 72° C. (in FIG. 2, the ordinate where DPG concentration=0%). On the other hand, when dipropylene glycol was added to the water in which the mixture is dissolved, a lamellar liquid crystal phase was formed at a lower temperature than 72° C., and a lamellar liquid crystal-dispersed phase, instead of a lamellar liquid crystal phase, was eventually formed (range where the concentration of dipropylene glycol is about 20-50%). The percentage of lamellar liquid crystals in the lamellar liquid crystal-dispersed phase decreased with an increase of the concentration of dipropylene glycol. When the concentration of dipropylene glycol was higher than about 50%, a bicontinuous microemulsion phase that does not contain lamellar liquid crystals was found to be formed at about 64° C. or higher.

The black circles in FIG. 2 are known to be, as a result of X-ray diffraction, a thermal change due to the crystallization of behenyl alcohol.

Accordingly, it was clarified that behenyl alcohol and sodium N-stearoyl methyl taurine do not form α-gel in an aqueous solution containing 50-80 mass % of dipropylene glycol, at about 64° C. or higher, and can form a low-viscosity liquid phase consisting of a lamellar liquid crystal-dispersed phase or a bicontinuous microemulsion phase.

In addition, the analysis results by varying the mixing ratio of the above-described (A) and (B) (80° C.) are shown in FIG. 3. The shaded region in FIG. 3 is the area of a bicontinuous microemulsion phase or a lamellar liquid crystal-dispersed phase. It was confirmed from the results that even when the content of behenyl alcohol and sodium N-stearoyl methyl taurine (mole ratio: 3:1) was increased to 80 mass %, a low-viscosity liquid phase without α-gel could be obtained.

Example 2: Induction of the Formation of α-Gel from a Bicontinuous Microemulsion Phase Next, the induction conditions for the formation of α-gel were investigated for the low-viscosity liquid phase without α-gel that was obtained in Example 1.

The composition indicated by the arrow in FIG. 2 (namely, Test Composition 1 prepared by using (B) dipropylene glycol:water=6:4 (mass ratio)) became a waxy solid at room temperature. The composition was reverted to a liquid phase by heating to 80° C. after storing for a few weeks at room temperature. The liquid phase was formed of a bicontinuous microemulsion phase, and the presence of α-gel was not observed. To this liquid phase, 8 times by mass of ion-exchanged water at room temperature was added and mixed with stirring, and then X-ray diffraction was carried out; the results are shown in FIG. 4. According to FIG. 4, multiple peaks corresponding to the long spacing were detected in the small-angle region, and a sharp single peak corresponding to the short spacing of about 0.42 nm was detected in the wide-angle region; thus it was shown that α-gel was formed in the composition.

Accordingly, it was shown that the formation of α-gel could easily be induced by diluting the bicontinuous microemulsion phase, which was formed of behenyl alcohol and sodium N-stearoyl methyl taurine in the dipropylene glycol aqueous solution, with water at room temperature.

Thus, it was shown that a low-viscosity liquid phase consisting of the above-described bicontinuous microemulsion phase is an "α-gel intermediate composition", which generates α-gel by the dilution with water at around room temperature, and the α-gel intermediate composition can be stably stored as a solid at room temperature. In the present application, the low-viscosity liquid phase consisting of the above-described lamellar liquid crystal-dispersed phase was also confirmed to be an "α-gel intermediate composition" (for example, Test Examples 5 and 7 of the present application).

Example 3: Investigation of Water-Soluable Solvents

Subsequently, kinds of materials that are added to the above-described water were investigated. The below-described Test Composition 2 was prepared by using eight kinds of water-soluble solvents that are structurally similar to dipropylene glycol and blendable in cosmetics, and the phase states at 80° C. and room temperature were determined according to the above-described criteria. The results are shown in Table 1. In the following tables (Tables 1 to 9), the phase state at 80° C. was expressed by the below-described symbols.

◉: bicontinuous microemulsion phase
○: lamellar liquid crystal-dispersed phase
x: phase other than the bicontinuous microemulsion phase or lamellar liquid crystal-dispersed phase <Formulation/method of preparation for Test Composition 2>

The below-described 30 mass % of (A) and 70 mass % of (B) were mixed, heated to 80° C., and mixed with stirring.
(A) Mixture of Behenyl alcohol:sodium N-stearoyl methyl taurine=3:1 (mole ratio)
(B) Mixture of a water-soluble solvent of Test Examples 1 to 8:water=7:3 (mass ratio)

TABLE 1

| | Test Example | | | | | | | |
|---|---|---|---|---|---|---|---|---|
| | 1 | 2 | 3 | 4 | 5 | 6 | 7 | 8 |
| water-soluble solvent | Propylene glycol monopropyl ether | 3-methoxy-1-butanol | Dipropylene glycol | Isoprene glycol | 1,3-butanediol | PEG-200 | Propylene glycol | Glycerin |
| IOB | 1.00 | 1.20 | 1.80 | 2.20 | 2.50 | 2.92 | 3.33 | 5.00 |
| Viscosity* (mPa·s) | 1.9 | 2.9 | 75.0 | 250.0 | 95.0 | 50.0 | 56.0 | 14.1 |
| Phase state of Test Composition 2 | | | | | | | | |
| 80° C. | ◉ | ◉ | ◉ | ◉ | ○ | ◉ | ○ | X |
| Room temperature | single-phase transparent liquid | single-phase transparent liquid | W-state solid | W-state solid | W-state solid | W-state solid | W-state solid | Separated |

*The value represents the viscosity at 25° C. except for isoprene glycol and propylene glycol, which measured at 20° C.

As shown in Table 1, when propylene glycol monopropyl ether, 3-methoxy-1-butanol, dipropylene glycol, isoprene glycol, 1,3-butanediol, PEG-200, or propylene glycol was used as the above-described water-soluble solvent, a liquid phase consisting of a bicontinuous microemulsion phase or a lamellar liquid crystal-dispersed phase was obtained at 80° C. (Test Examples 1 to 7). However, when glycerin was used, separation to a solid and a liquid took place (Test Example 8). The difference of water-soluble solvents in Test Examples 1 to 7 and a water-soluble solvent in Test Example 8 was investigated. They are indistinguishable by many properties (for example, viscosity etc.); however, if the polarity is focused, they can be distinguished into the following two groups. That is, when a water-soluble solvent heating at 80° C. was added while stirring with a homogenizer. Then, the emulsification was carried out by gradually adding ion-exchanged water (80 g) at room temperature while stirring the mixture with a homogenizer; thus an O/W emulsion cosmetic was obtained.

<Emulsion Stability>

The above-described emulsion cosmetics were stored, in a constant-temperature bath at 25° C., for 1 week, and then the below-described states were determined visually.

◯: None of creaming, aggregation, or phase separation was observed.

x: One of creaming, aggregation, or phase separation was observed.

TABLE 2

| | Test Example | | | | | | | |
|---|---|---|---|---|---|---|---|---|
| | 1 | 2 | 3 | 4 | 5 | 6 | 7 | 8 |
| Water-soluble solvent | Propylene glycol monopropyl ether | 3-methoxy-1-butanol | Dipropylene glycol | Isoprene glycol | 1,3-butanediol | PEG-200 | Propylene glycol | Glycerin |
| IOB | 1.00 | 1.20 | 1.80 | 2.20 | 2.50 | 2.92 | 3.33 | 5.00 |
| | Evaluation of the emulsion cosmetics | | | | | | | |
| Phase state | O/W | O/W | O/W | O/W | O/W | O/W | O/W | Separated |
| Emulsion stability | x | x | ◯ | ◯ | ◯ | ◯ | ◯ | x | with the IOB value of 1.00 to 3.33 (Test Examples 1 to 7) was used, a bicontinuous microemulsion phase or a lamellar liquid crystal-dispersed phase was formed; when glycerin with the IOB of 5.00 was used, separation to a solid and a liquid took place (Test Example 8).

Accordingly, it was suggested from the above-described results that maintaining the polarity of the solvent within a certain range is useful to inhibit the formation of α-gel from a higher alcohol having 16 or more carbon atoms and an anionic surfactant and to form a bicontinuous microemulsion phase or a lamellar liquid crystal-dispersed phase.

Furthermore, the above-described Test Composition 2 was cooled to room temperature and the material state was investigated. The composition prepared by using a water-soluble solvent with the IOB value of 1.80 to 3.33 became a white waxy solid (Test Examples 3 to 7). The composition prepared by using propylene glycol monopropyl ether (IOB value=1.00), which has the IOB value lower than the above-described range, or 3-methoxy-1-butanol (IOB value=1.20) stayed being a single-phase transparent liquid (Test Examples 1 and 2).

Thus, it was clarified that in order to prepare an α-gel intermediate composition storable at room temperature over a long period, we may dissolve a higher alcohol having 16 or more carbon atoms and an anionic surfactant, with a suitable mole ratio (specifically, 3:2 to 5:1) for the formation of α-gel, in an aqueous solution of an water-soluble solvent with the IOB value of 1.5 to 3.5 (for example, dipropylene glycol, isoprene glycol, 1,3-butanediol, PEG-200, propylene glycol, etc.).

Example 4: Investigation of Emulsion Stability of α-Gel-Containing Emulsion Cosmetics In addition, O/W emulsion cosmetics were prepared by using Test Composition 2 prepared in Example 3, and the emulsion stability of the cosmetics were evaluated.
<Production Method of Emulsion Cosmetics>

Test Composition 2 (10 g) prepared in Example 3 was heated to 80° C., and liquid paraffin (10 g) dissolved by As shown in Table 2, heated oil and water at room temperature were sequentially added to Test Composition 2 prepared by using dipropylene glycol, isoprene glycol, 1,3-butanediol, PEG-200, or propylene glycol aqueous solution, and an O/W emulsion cosmetic excellent in emulsion stability was obtained by mixing with stirring (Test Examples 3 to 7). On the other hand, an O/W emulsion cosmetic was obtained from Test Composition 2 prepared by using propylene glycol monopropyl ether or 3-methoxy-1-butanol aqueous solution; however, the emulsion stability was not satisfactory (Test Examples 1 and 2). From Test Composition 2 of Test Example 8, which separated into two phases, an emulsion could not be obtained. As a result of X-ray diffraction, the presence of α-gel was confirmed for the emulsion cosmetics of Test Examples 3 to 7.

Accordingly, a composition consisting of a higher alcohol having 16 or more carbon atoms and an anionic surfactant, with the mole ratio suitable for the formation of α-gel (specifically, 3:2 to 5:1), and an aqueous solution of a water-soluble solvent with the IOB value of 1.5 to 3.5 (for example, dipropylene glycol, isoprene glycol, 1,3-butanediol, PEG-200, propylene glycol, etc.); and forms a liquid consisting of a bicontinuous microemulsion phase or a lamellar liquid crystal-dispersed phase under a high temperature (for example, 65 to 80° C.) and becomes a solid at room temperature (namely, α-gel intermediate composition of the present invention) was shown to be usable as the intermediate composition to prepare an α-gel-containing O/W emulsion cosmetic that is excellent in emulsion stability.

Example 5: Investigation of Kinds of Anionic Surfactants

Next, an investigation was carried out by varying the kinds of anionic surfactants. In the above-described Test Composition 2, sodium N-stearoyl glutamate (Table 3) or sodium monostearyl phosphate (Table 4) was used instead of sodium N-stearoyl methyl taurine to prepare test compositions, and similar analyses were carried out.

TABLE 3

Anionic surfactant: Sodium N-stearoyl glutamate

| | Test Examples | | | | | | | |
|---|---|---|---|---|---|---|---|---|
| | 9 | 10 | 11 | 12 | 13 | 14 | 15 | 16 |
| Water-soluble solvent | Propylene glycol monopropyl ether | 3-methoxy-1-butanol | Dipropylene glycol | Isoprene glycol | 1,3-butanediol | PEG-200 | Propylene glycol | Glycerin |
| IOB | 1.00 | 1.20 | 1.80 | 2.20 | 2.50 | 2.92 | 3.33 | 5.00 |
| | Phase state of the intermediate composition | | | | | | | |
| 80° C. Room temperature | ◎ single-phase transparent liquid | ◎ single-phase transparent liquid | ◎ W-state solid | ◎ W-state solid | ◎ W-state solid | ○ W-state solid | ○ W-state solid | X Separated |
| | Evaluation of the emulsion cosmetics | | | | | | | |
| Phase state | O/W | O/W | O/W | O/W | O/W | O/W | O/W | Separated |
| Emulsion stability | X | X | ○ | ○ | ○ | ○ | ○ | X |

TABLE 4

Anionic surfactant: Sodium monostearyl phosphate

| | Test Examples | | | | | | | |
|---|---|---|---|---|---|---|---|---|
| | 17 | 18 | 19 | 20 | 21 | 22 | 23 | 24 |
| Water-soluble solvent | Propylene glycol monoprapyl ether | 3-methoxy-1-butanol | Dipropylene glycol | Isoprene glycol | 1,3-butanediol | PEG-200 | Propylene glycol | Glycerin |
| IOB | 1.00 | 1.20 | 1.80 | 2.20 | 2.50 | 2.92 | 3.33 | 5.00 |
| | Phase state of the intemediate composition | | | | | | | |
| 80° C. Room temperature | ◎ single-phase transparent liquid | ◎ single-phase transparent liquid | ◎ W-state solid | ◎ W-state solid | ◎ W-state solid | ◎ W-state solid | ◎ W-state solid | X Separated |
| | Evaluation of the emulsion cosmetics | | | | | | | |
| Phase state | O/W | O/W | O/W | O/W | O/W | O/W | O/W | Separated |
| Emulsion stability | X | X | ○ | ○ | ○ | ○ | ○ | X |

From Table 3 and Table 4, even when sodium N-stearoyl glutamate (Table 3) or sodium monostearyl phosphate (Table 4) is used as the anionic surfactant, by using 70 mass % aqueous solution of a water-soluble solvent with the IOB value of 1.5 to 3.5 as the solvent, an α-gel intermediate composition, which becomes a liquid consisting of a bicontinuous microemulsion phase or a lamellar liquid crystal-dispersed phase under a high temperature and a solid at room temperature, can be obtained (Test Examples 11 to 15 and Test Examples 19 to 23). And an α-gel-containing O/W-type emulsion composition excellent in emulsion stability is confirmed to be obtained by sequentially adding heated oil and water at room temperature to the intermediate composition and by mixing with stirring (Test Examples 11 to 15 and Test Examples 19 to 23).

Example 6: Investigation of Concentration of Water-Soluable Solvents

In the above-described Examples 2 to 5, the concentration of a water-soluble solvent was fixed at 70 mass %; thus an investigation was carried out at other concentrations (specifically, 50 to 80 mass %). The results are shown in Tables 5 to 9.

TABLE 5

Water-soluble solvent: Isoprene glycol (IOB = 2.20)

| | | Anionic surfactant | | | | | | | |
|---|---|---|---|---|---|---|---|---|---|
| | | Sodium N-stearoyl methyl taurine | | | | Sodium monostearyl phosphate | | | |
| | | Test Example | | | | | | | |
| | | 25 | 26 | 4 | 27 | 28 | 29 | 20 | 30 |
| | | Concentration of the water-soluble solvent | | | | | | | |
| | | 50% | 60% | 70% | 80% | 50% | 60% | 70% | 80% |
| Intermediate composition | 80° C. Room temperature | ◎ W-state solid | ◎ W-state solid | ◎ W-state solid | ◎ W-state solid | ○ W-state solid | ◎ W-state solid | ◎ W-state solid | ◎ W-state solid |

TABLE 5-continued

| | | Water-soluble solvent: Isoprene glycol (IOB = 2.20) | | | | | | | |
|---|---|---|---|---|---|---|---|---|---|
| | | Anionic surfactant | | | | | | | |
| | | Sodium N-stearoyl methyl taurine | | | | Sodium monostearyl phosphate | | | |
| | | Test Example | | | | | | | |
| | | 25 | 26 | 4 | 27 | 28 | 29 | 20 | 30 |
| | | Concentration of the water-soluble solvent | | | | | | | |
| | | 50% | 60% | 70% | 80% | 50% | 60% | 70% | 80% |
| Emulsion cosmetics | Phase state | O/W | O/W | O/W | O/W | O/W | O/W | O/W | O/W |
| | Emulsion stability | ○ | ○ | ○ | ○ | ○ | ○ | ○ | ○ |

TABLE 6

| | | Water-soluble solvent: Dipropylene glycol (IOB = 1.80) | | | | | | |
|---|---|---|---|---|---|---|---|---|
| | | Anionic surfactant | | | | | | |
| | | Sodium N-stearoyl methyl taurine | | Sodium N-stearoyl glutamate | | Sodium monostearyl phosphate | | |
| | | Test Example | | | | | | |
| | | 31 | 32 | 33 | 34 | 35 | 36 | 37 |
| | | Concentration of the water-soluble solvent | | | | | | |
| | | 60% | 80% | 60% | 80% | 50% | 60% | 80% |
| Intermediate composition | 80° C. | ◎ | ◎ | ◎ | ◎ | ○ | ◎ | ◎ |
| | Room temperature | W-state solid | W-state solid | W-state solid | W-state solid | W-state solid | W-state solid | W-state solid |
| Emulsion cosmetics | Phase state | O/W | O/W | O/W | O/W | O/W | O/W | O/W |
| | Emulsion stability | ○ | ○ | ○ | ○ | ○ | ○ | ○ |

TABLE 7

| | | Water-soluble solvent: 1,3-butanediol (IOB = 2.50) | | | | | |
|---|---|---|---|---|---|---|---|
| | | Anionic surfactant | | | | | |
| | | Sodium N-stearoyl methyl taurine | | Sodium N-stearoyl glutamate | | Sodium monostearyl phosphate | |
| | | Test Example | | | | | |
| | | 38 | 39 | 40 | 41 | 42 | 43 |
| | | Concentration of the water-soluble solvent | | | | | |
| | | 50% | 60% | 50% | 60% | 50% | 60% |
| Intermediate composition | 80° C. | ○ | ○ | ○ | ○ | ○ | ◎ |
| | Room temperature | W-state solid | W-state solid | W-state solid | W-state solid | W-state solid | W-state solid |
| Emulsion cosmetics | Phase state | O/W | O/W | O/W | O/W | O/W | O/W |
| | Emulsion stability | ○ | ○ | ○ | ○ | ○ | ○ |

TABLE 8

Water-soluble solvent: PEG-200 (IOB = 2.92)

| | | Anionic surfactant | | | | | |
|---|---|---|---|---|---|---|---|
| | | Sodium N-stearoyl methyl taurine | | Sodium N-stearoyl glutamate | | Sodium monostearyl phosphate | |
| | | Test Example | | | | | |
| | | 44 | 45 | 46 | 47 | 48 | 49 |
| | | Concentration of the water-soluble solvent | | | | | |
| | | 60% | 80% | 60% | 80% | 60% | 80% |
| Intermediate composition | 80° C. | ○ | ◎ | ○ | ◎ | ◎ | ◎ |
| | Room temperature | W-state solid | W-state solid | W-state solid | W-state solid | W-state solid | W-state solid |
| Emulsion cosmetics | Phase state | O/W | O/W | O/W | O/W | O/W | O/W |
| | Emulsion stability | ○ | ○ | ○ | ○ | ○ | ○ |

TABLE 9

Water soluble solvent: Propylene glycol (IOB = 3.33)

| | | Anionic surfactant | | | | | |
|---|---|---|---|---|---|---|---|
| | | Sodium N-stearoyl methyl taurine | | Sodium N-stearoyl glutamate | | Sodium monostearyl phosphate | |
| | | Test Example | | | | | |
| | | 7 | 50 | 15 | 51 | 23 | 52 |
| | | Concentration of the water-soluble solvent | | | | | |
| | | 70% | 80% | 70% | 80% | 70% | 80% |
| Intermediate composition | 80° C. | ○ | ◎ | ○ | ◎ | ◎ | ◎ |
| | Room temperature | W-state solid | W-state solid | W-state solid | W-state solid | W-state solid | W-state solid |
| Emulsion cosmetics | Phase state | O/W | O/W | O/W | O/W | O/W | O/W |
| | Emulsion stability | ○ | ○ | ○ | ○ | ○ | ○ |

As shown in Tables 5 to 9 (Test Examples 25 to 52), isoprene glycol, dipropylene glycol, 1,3-butanediol, PEG-200, or propylene glycol, in the range of 50 to 80 mass % aqueous solution, can provide a low-viscosity liquid phase consisting of a bicontinuous microemulsion phase or a dispersed liquid crystal phase by dissolving a higher alcohol having 16 or more carbon atoms and an anionic surfactant, and the low-viscosity liquid phase can become a solid that can be stored for a long term at room temperature. And it was confirmed that α-gel-containing O/W emulsion excellent in emulsion stability can be obtained by sequentially adding heated oil and an aqueous phase at room temperature to the low-viscosity liquid phase and by mixing with stirring.

In Test Composition 2 described thus far, the mixing ratio of (A) a mixture containing a higher alcohol having 16 or more carbon atoms and an anionic surfactant in the mole ratio of 3:1 and (B) a mixture containing a water-soluble solvent with the IOB value of 1.80 to 3.33 and water in the mass ratio of 7:3 was fixed at (A):(B)=30:70 (mass ratio); however, similar results were also obtained in a wide range of the mixing ratio (A):(B)=20:80 to 80:20.

Thus, it was clarified that when a mixture containing a water-soluble solvent with the IOB value of 1.5 to 3.5 and water in the mass ratio of 5:5 to 8:2 is used as the solvent, a higher alcohol having 16 or more carbon atoms and an anionic surfactant (though mixed in the mole ratio where α-gel can be easily formed) form a bicontinuous microemulsion phase or a dispersed liquid crystal phase instead of α-gel and can become a low-viscosity liquid. And it was shown that, by adding oil at 85° C. or lower to the liquid phase and subsequently diluting with water at room temperature, an α-gel-containing O/W emulsion cosmetic, in which the surrounding of the oil phase is covered with α-gel and thus having excellent emulsion stability, could be stably obtained.

Thus, the α-gel intermediate composition of the present invention is an intermediate composition that can easily generate an α-gel-containing O/W emulsion cosmetic excellent in emulsion stability by adding heated oil and diluting with water at room temperature.

Example 7: Investigation of Viscosity Stability

As described above, a big issue has been present for the past α-gel-containing O/W emulsion cosmetic in that the viscosity gradually increases over time. Thus, the viscosity stability of the α-gel-containing O/W emulsion cosmetic prepared by the method of the present invention was compared with the α-gel-containing O/W emulsion cosmetic, of the identical formulation, prepared by the conventional method.

<Formulation>

| Components | Blending quantity (mass %) |
| --- | --- |
| Behenyl alcohol | 3.3 |
| Stearyl alcohol | 0.9 |
| Liquid paraffin | 6.0 |
| Glyceryl tri-2-ethylhexanoate | 4.0 |
| Sodium N-stearoyl methyl taurine | 1.2 |
| Dipropylene glycol | 6.5 |
| Glycerin | 9.0 |
| 1,3-Butylene glycol | 5.0 |
| Phenoxyethanol | 0.5 |
| Citric acid | 0.02 |
| Sodium citrate | 0.08 |
| Ion-exchanged water | 63.5 |

Test Example 53: Production Method of the Present Invention

The entire components of the below-described (1) α-gel intermediate composition were dissolved at 80° C., and a liquid phase consisting of a colorless, transparent, bicontinuous microemulsion phase was obtained. While stirring the liquid phase with a homogenizer, the below-described (2) oil and oil components (namely, oil phase) dissolved by heating at 80° C. were added, and subsequently the below-described (3) water and aqueous components (namely, the main aqueous phase) that were premixed at room temperature were added little by little. After the completion of addition, deaeration was carried out and an O/W emulsion cream was obtained.

| Components | Blending quantity (mass %) |
| --- | --- |
| (1) α-Gel intermediate composition | |
| Behenyl alcohol | 3.3 |
| Stearyl alcohol | 0.9 |
| Sodium N-stearoyl methyl taurine | 1.2 |
| Dipropylene glycol | 6.5 |
| Ion-exchanged water | 1.5 |
| (2) Oil and oil components (oil phase) | |
| Liquid paraffin | 6.0 |
| Glyceryl tri-2-ethylhexanoate | 4.0 |
| (3) Water and aqueous components (main aqueous phase) | |
| Glycerin | 9.0 |
| 1,3-Butylene glycol | 5.0 |
| Phenoxyethanol | 0.5 |
| Citric acid | 0.02 |
| Sodium citrate | 0.08 |
| Ion-exchanged water | 62.0 |

Test Example 54: Conventional Production Method (Comparative Example)

The emulsification was carried out by adding the below-described (1) oil and oil components (namely, oil phase) dissolved at 70° C. to the below-described (2) water and aqueous components dissolved by heating at 70° C. (namely, aqueous phase) while stirring the aqueous phase with a homogenizer. Immediately after emulsification, it was cooled to 25° C. while stirring in an ice bath. Then, deaeration was carried out, and an O/W emulsion cream was obtained.

| Components | Blending quantity (mass %) |
| --- | --- |
| (1) Oil and oil components (oil phase) | |
| Behenyl alcohol | 3.3 |
| Stearyl alcohol | 0.9 |
| Liquid paraffin | 6.0 |
| Glyceryl tri-2-ethylhexanoate | 4.0 |
| (2) Water and aqueous components (aqueous phase) | |
| Sodium N-stearoyl methyl taurine | 1.2 |
| Dipropylene glycol | 6.5 |
| Glycerin | 9.0 |
| 1,3-Butylene glycol | 5.0 |
| Phenoxyethanol | 0.5 |
| Citric acid | 0.02 |
| Sodium citrate | 0.08 |
| Ion-exchanged water | 63.5 |

<Test of Viscosity Stability>

Two kinds of α-gel-containing O/W emulsion cosmetics prepared by the above-described method were stored at 0° C., 25° C., 37° C., or 50° C. for 2 months. Immediately after production, after 1 month, and after 2 months, portions of the respective cosmetics were collected and kept warm at 30° C. for 30 minutes. Then, the viscosity was measured with a B-type rotational viscometer (Vismetron viscometer, manufactured by Shibaura Systems Co., Ltd.) (Rotor No. 3, 0.3 or 0.6 rpm, 5 minutes). The results are shown in Table 10.

TABLE 10

| | | Viscosity stored at each temperature (mPa · s) | | | |
| --- | --- | --- | --- | --- | --- |
| Production method | Storage period | 0° C. | 25° C. | 37° C. | 50° C. |
| The present invention method (Test example 53) | No storage (immediately after production) | 253200 (100.0%) | 253200 (100.0%) | 253200 (100.0%) | 253200 (100.0%) |
| | 1 month | 244800 (96.7%) | 259200 (102.4%) | 246000 (97.2%) | 238200 (94.1%) |
| | 2 months | 255800 (101.0%) | 261400 (103.2%) | 254200 (100.4%) | 243200 (96.1%) |
| Conventional method (Test example 54) | No storage | 74500 (100.0%) | 74500 (100.0%) | 74500 (100.0%) | 74500 (100.0%) |
| | 1 month | 175800 (236.0%) | 200800 (269.5%) | 154300 (207.1%) | 146000 (196.0%) |
| | 2 months | 253800 (340.7%) | 302500 (406.0%) | 186500 (250.3%) | 176300 (236.6%) |

As shown in Table 10, the viscosity of the cream prepared by the conventional method increased significantly, when stored at any temperature of 0 to 50° C., about 2.0 to 2.7 times after 1 month and about 2.4 to 4.1 times after 2 months. On the other hand, the viscosity of the cream prepared by the method of the present invention hardly increased under any temperature of 0 to 50° C. Even in the highest case, the increase was only 3.2% (stored at 25° C. for 2 months). This high viscosity stability is not conceivable from the past common sense for α-gel-containing O/W-type emulsion cosmetics.

Thus, its cause was investigated. When the viscosity immediately after the production was compared, the cream prepared by the method of the present invention, regardless of the identical formulation, had about 3.4 times viscosity of the cream prepared by the conventional method. Accordingly, if prepared by the method of the present invention, the formation reaction of α-gel is almost completed at the time of emulsion production, and the new formation reaction of α-gel may not take place later (therefore, the viscosity does not increase).

Furthermore, it was clarified that if the emulsion is prepared by the method of the present invention, an emulsion having very small particle sizes is obtained. Micrographs taken immediately after the production of the above-described α-gel-containing O/W emulsion cosmetics prepared by the production method of the present invention (Test Example 53) and by the conventional production method (Test Example 54) are shown in FIG. 5 (top and bottom two micrographs on the left column). The average emulsion particle size of the cosmetic obtained by the production method of the present invention was about 500 nm; on the other hand, that of the cosmetic prepared by the conventional production method was about 3 μm.

The micrograph shown on the right column of the conventional method is an example where aggregated masses were generated because the cooling rate after emulsification was too fast in the conventional method (though the formulations are identical). Thus, it has been difficult to satisfactorily control the quality of products by the conventional production method of α-gel-containing O/W emulsion cosmetics.

Thus, it was shown that, a low-viscosity liquid consisting of a bicontinuous microemulsion phase or a dispersed liquid crystal phase (namely, the α-gel intermediate composition of the present invention) obtained by mixing, with heating at 65 to 85° C., (A) a mixture of a higher alcohol having 16 or more carbon atoms and an anionic surfactant (mole ratio: 3:2 to 5:1) and (B) a mixture of a water-soluble solvent with the IOB value of 1.5 to 3.5 and water (mass ratio: 5:5 to 8:2) is an intermediate composition to easily and stably prepare an α-gel-containing O/W emulsion cosmetic excellent in emulsion stability and viscosity stability. The method for use is a very simple in that the intermediate composition is heated to 65 to 85° C., oil heated to 85° C. or lower is added while stirring, and it is subsequently diluted, about 3 to 50 times by mass, by gradually adding water at 30° C. or lower. Although the method is exceedingly simple compared with the conventional method, the emulsion stability of the α-gel-containing O/W emulsion cosmetic prepared by the present method is very high. In addition, it has unprecedented merits in that the viscosity increase over time is hardly observed.

Industrial Applicability

The α-gel intermediate composition of the present invention enables the preparation of an α-gel-containing O/W emulsion cosmetic excellent in emulsion stability and viscosity stability by only adding heated oil to the heated composition and then diluting with water at room temperature. In addition, the intermediate composition can be stably stored, as a waxy solid, at room temperature over a long period. Therefore, industrial application values, such as the cost reduction by bulk preparation and the commercialization as an intermediate composition, are very high.

Hereinafter, examples of the water-in-oil emulsion cosmetic of the present invention will be illustrated. It is to be understood that the present invention is not limited by these examples.

Example 8: Milky Lotion

| Components | Blending quantity (mass %) |
| --- | --- |
| (1) Sodium N-stearoyl methyl taurine | 0.4 |
| (2) Behenyl alcohol | 1.1 |
| (3) Stearyl alcohol | 0.3 |
| (4) Dipropylene glycol | 5.0 |
| (5) Ion-exchanged water | 3.0 |
| (6) Perfumes | 0.1 |
| (7) Pentaerythritol tetra-2-ethylhexanoate | 2.0 |
| (8) α-olefin oligomer | 3.0 |
| (9) Dimethylpolysiloxane (KF-96A-6cs, manufactured by Shin-Etsu Chemical Co., Ltd.) | 2.0 |
| (10) Purified vaseline | 1.0 |
| (11) 1,3-Butylene glycol | 2.0 |
| (12) Phenoxyethanol | 0.5 |
| (13) Glycerin | 4.0 |
| (14) Carboxyvinylpolymer | 0.03 |
| (15) Potassium hydroxide | 0.01 |
| (16) Tranexamic acid | 0.1 |
| (17) Citric acid | 0.02 |
| (18) Sodium citrate | 0.08 |
| (19) Ion-exchanged water | balance |

(Preparation Method)

A bicontinuous microemulsion was obtained by mixing with stirring components (1) to (5) at 80° C., and then oil and oil components (6) to (10) dissolved in advance at 80° C. were gradually added while stirring with a homogenizer. To the mixture, water and aqueous components (11) to (19) premixed at room temperature were slowly poured while stirring, and a milky lotion was obtained. The obtained milky lotion had extremely good viscosity stability compared with the milky lotion prepared by the conventional method (after emulsification by adding oil and oil components (=(2), (3), and (6) to (10)) dissolved by heating at 70° C. to water and aqueous components (=(1), (4), (5), and (11) to (19)) dissolved by heating at 70° C., cooling to 25° C. was carried out with an Onlator® (Sakura Seisakusho Ltd.)).

Example 9: Milky Lotion

| Components | Blending quantity (mass %) |
| --- | --- |
| (1) Sodium N-stearoyl methyl taurine | 0.6 |
| (2) Behenyl alcohol | 1.3 |
| (3) 1,3-Butylene glycol | 6.0 |
| (4) Ion-exchanged water | 2.0 |
| (5) Perfumes | 0.05 |
| (6) Dimethylpolysiloxane (KF-96A-6cs, manufactured by Shin-Etsu Chemical Co., Ltd.) | 2.0 |
| (7) Squalane | 4.0 |

-continued

| Components | Blending quantity (mass %) |
|---|---|
| (8) Cetyl isostearate | 0.6 |
| (9) Glycerin | 5.0 |
| (10) Carboxyvinylpolymer | 1.0 |
| (11) Potassium hydroxide | 0.3 |
| (12) Chamomile extract | 0.1 |
| (13) Ion-exchanged water | balance |

(Preparation Method)

A lamellar liquid crystal dispersion was obtained by mixing with stirring components (1) to (4) at 85° C., and then oil and oil components (5) to (8) dissolved in advance by heating at 80° C. were gradually added while stirring with a homogenizer. To the mixture, water and aqueous components (9) to (13) premixed at room temperature were slowly poured while stirring, and a milky lotion was obtained. The obtained milky lotion had extremely good viscosity stability compared with the milky lotion prepared by the conventional method (after emulsification by adding oil and oil components (=(2) and (5) to (8)) dissolved by heating at 70° C. to water and aqueous components (=(1), (3), (4), and (9) to (13)) dissolved by heating at 70° C., cooling to 25° C. was carried out with an Onlator).

Example 10: Milky Lotion

| Components | Blending quantity (mass %) |
|---|---|
| (1) Sodium monostearyl phosphate | 0.8 |
| (2) Stearyl alcohol | 1.5 |
| (3) Isoprene glycol | 4.5 |
| (4) 1,4-butanediol | 1.5 |
| (5) Ion-exchanged water | 1.5 |
| (6) Perfumes | 0.09 |
| (7) Glyceryl tristearate | 2.5 |
| (8) Squalane | 4.5 |
| (9) Dimethylpolysiloxane (KF-96A-6cs, manufactured by Shin-Etsu Chemical Co., Ltd.) | 2.0 |
| (10) Dipropylene glycol | 7.0 |
| (11) Erythritol | 1.3 |
| (12) Glycerin | 4.0 |
| (13) Phenoxyethanol | 0.3 |
| (14) Xanthan gum | 0.5 |
| (15) Sodium hexametaphosphate | 0.03 |
| (16) Ion-exchanged water | balance |

(Preparation Method)

A bicontinuous microemulsion was obtained by mixing with stirring components (1) to (5) at 80° C., and then oil and oil components (6) to (9) mixed in advance at 50° C. were gradually added while stirring with a homogenizer. To the mixture, water and aqueous components (10) to (16) premixed at room temperature were slowly poured while stirring, and a milky lotion was obtained. The obtained milky lotion had extremely good viscosity stability compared with the milky lotion prepared by the conventional method (after emulsification by adding oil and oil components (=(2) and (6) to (10)) dissolved by heating at 70° C. to water and aqueous components (=(1), (3) to (5), and (10) to (16)) dissolved by heating at 70° C., cooling to 25° C. was carried out with an Onlator).

Example 11: Sunscreen Cream

| Components | Blending quantity (mass %) |
|---|---|
| (1) Sodium N-stearoyl methyl taurine | 1.2 |
| (2) Behenyl alcohol | 3.3 |
| (3) Stearyl alcohol | 0.9 |
| (4) Dipropylene glycol | 6.0 |
| (5) Ion-exchanged water | 2.0 |
| (6) Perfume | 0.08 |
| (7) Glyceryl tri-2-ethylhexanoate | 2.0 |
| (8) Bis(2-ethylhexyl) succinate | 3.0 |
| (9) 2-Ethylhexyl p-methoxycinnamate | 5.0 |
| (10) Avobenzone | 3.0 |
| (11) Bis-ethylhexyloxyphenol methoxyphenyl triazine | 1.0 |
| (12) 1,3-Butylene glycol | 5.0 |
| (13) Phenoxyethanol | 0.5 |
| (14) Glycerin | 9.0 |
| (15) EDTA trisodium salt | 0.1 |
| (16) Erythritol | 0.1 |
| (17) Citric acid | 0.02 |
| (18) Sodium citrate | 0.08 |
| (19) Ion-exchanged water | balance |

(Preparation Method)

A bicontinuous microemulsion was obtained by mixing with stirring components (1) to (5) at 80° C., and then oil and oil components (6) to (11) mixed in advance at 70° C. were gradually added while stirring with a homogenizer. To the mixture, water and aqueous components (12) to (19) premixed at room temperature were slowly poured while stirring, and a sunscreen cream was obtained. The obtained sunscreen cream had extremely good viscosity stability compared with the sunscreen cream prepared by the conventional method (after emulsification by adding oil and oil components (=(2), (3), and (6) to (11)) dissolved by heating at 70° C. to water and aqueous components (=(1), (4), (5), and (12) to (19)) dissolved by heating at 70° C., cooling to 25° C. was carried out with an Onlator).

Example 12: Cream

| Components | Blending quantity (mass %) |
|---|---|
| (1) Sodium N-stearoyl methyl taurine | 1.3 |
| (2) Behenyl alcohol | 2.0 |
| (3) 1,3-Butylene glycol | 6.5 |
| (4) Ion-exchanged water | 1.5 |
| (5) Perfumes | 0.05 |
| (6) Dimethylpolysiloxane (KF-96A-6cs, manufactured by Shin-Etsu Chemical Co., Ltd.) | 7.4 |
| (7) Squalane | 4.0 |
| (8) Behenyl alcohol | 0.6 |
| (9) Purified vaseline | 1.0 |
| (10) Dipropylene glycol | 5.0 |
| (11) Phenoxyethanol | 0.5 |
| (12) Glycerin | 7.0 |
| (13) EDTA3Na | 0.1 |
| (14) Chamomile extract | 0.1 |
| (15) Citric acid | 0.02 |
| (16) Sodium citrate | 0.08 |
| (17) Ion-exchanged water | balance |

(Preparation Method)

A lamellar liquid crystal dispersion was obtained by mixing with stirring components (1) to (4) at 80° C., and then oil and oil components (5) to (9) mixed in advance at 80° C. were gradually added while stirring with a homogenizer. To the mixture, water and aqueous components (10) to (17) premixed at room temperature were slowly poured while stirring, and a cream was obtained. The obtained cream had extremely good viscosity stability compared with the cream prepared by the conventional method (after emulsification by adding oil and oil components (=(2) and (5) to (9)) dissolved by heating at 70° C. to water and aqueous components (=(1), (3), (4), and (10) to (17)) dissolved by heating at 70° C., cooling to 25° C. was carried out with an Onlator).

What is claimed is:

1. An α-gel intermediate composition consisting of:
   (A) 20 to 80 mass % of a mixture of one or more higher alcohols having 16 or more carbon atoms, and an anionic surfactant, in the mole ratio of 3:2 to 5:1, and
   (B) 20 to 80 mass % of a mixture of one or more water-soluble solvents having an IOB (inorganic organic balance) value of 1.5 to 3.5, and water, in the mass ratio of 5:5 to 8:2,
   wherein the anionic surfactant is one of more surfactants selected from the group consisting of N-acyl methyl taurine salts, N-acyl glutamic acid salts, and monoalkylphosphoric acid salts; and
   wherein the composition, when at 65 to 85° C., is a liquid bicontinuous microemulsion or a lamellar liquid crystal-dispersed bicontinuous microemulsion; and
   wherein the composition, when at room temperature, is a solid.

2. The α-gel intermediate composition according to claim 1, wherein:
   the water-soluble solvent having the IOB value of 1.5 to 3.5 is one or more water-soluble solvents selected from the group consisting of dipropylene glycol, isoprene glycol, 1,3-butanediol, polyethylene glycol, and propylene glycol.

* * * * *